United States Patent
Sorribes

(10) Patent No.: US 6,517,557 B1
(45) Date of Patent: Feb. 11, 2003

(54) INSTRUMENT AND USE OF INSTRUMENT FOR CORRECTING THE SHAPE OF AN EXTERNAL EAR

(76) Inventor: Michael Miravet Sorribes, Jyllingeparken 156, DK-4040 Jyllinge (DK)

(*) Notice: Subject to any disclaimer, the term of this patent is extended or adjusted under 35 U.S.C. 154(b) by 0 days.

(21) Appl. No.: 09/762,621

(22) PCT Filed: Aug. 12, 1998

(86) PCT No.: PCT/DK98/00346

§ 371 (c)(1),
(2), (4) Date: Feb. 9, 2001

(87) PCT Pub. No.: WO00/09050

PCT Pub. Date: Feb. 24, 2000

(51) Int. Cl.[7] ............................................. A61B 17/122
(52) U.S. Cl. ........................................... 606/151; 606/1
(58) Field of Search .......................... 606/1, 151, 120, 606/204.15; D11/42; 24/521, 517, 518; 128/452, 110

(56) References Cited

U.S. PATENT DOCUMENTS

| | | | | |
|---|---|---|---|---|
| 516,135 A | * | 3/1894 | Thamm | 128/76 |
| 543,455 A | * | 7/1895 | Weber | 128/76 |
| 1,050,744 A | * | 1/1913 | Monier-Williams | 606/204.15 |
| 1,062,654 A | * | 5/1913 | Lowman | 606/204.15 |
| 1,338,090 A | * | 8/1920 | Parvin | 606/204.15 |
| 2,040,083 A | * | 5/1936 | Elliot et al. | 63/14 |
| 2,339,572 A | * | 1/1944 | Jurovaty | 128/76 |
| 2,435,344 A | * | 2/1948 | Farkas | 63/14 |
| 2,447,350 A | * | 8/1948 | Levesque | 63/14 |
| D153,610 S | * | 5/1949 | Kline | D11/42 |
| 2,511,170 A | * | 6/1950 | McCann | 63/14 |
| 2,757,665 A | | 8/1956 | Tanikawa | |
| 2,882,702 A | * | 4/1959 | Goldberg et al. | 63/14 |
| 3,238,938 A | * | 3/1966 | Jurgovan | 128/76 |
| 3,958,430 A | | 5/1976 | Barron | |
| 4,185,471 A | * | 1/1980 | Saccoccio | 63/14 C |
| 4,187,838 A | | 2/1980 | Dubrowski | |
| 4,625,526 A | * | 12/1986 | Milawski | 63/2 |
| 4,694,664 A | * | 9/1987 | Elsener | 63/12 |

FOREIGN PATENT DOCUMENTS

| | | |
|---|---|---|
| CH | 207417 | 12/1939 |
| CH | 208142 C | 4/1940 |

* cited by examiner

Primary Examiner—John J. Calvert
Assistant Examiner—Alissa L. Hoey
(74) Attorney, Agent, or Firm—McCormick, Paulding & Huber LLP

(57) ABSTRACT

An instrument and use of an instrument serving for correcting the shape of an external ear, for example jug ears, lop ears, cop ears or Stahl's ears. Correction takes place by, from two sides, affecting a chosen zone of the ear for a period of time with forces for giving the cartilage of that zone a permanent deformation. The instrument comprises a matrix and a patrix interconnected by a hinge and made to, from each side, interactingly affect a chosen zone of the ear for a relatively long period of time with forces for giving the cartilage of that zone a permanent deformation. The hinge can by means of a screw be fixed in the correcting position until the deformation of the cartilage is permanent. A deformed ear can by means of the invention more easily and effectively than known per se be corrected non-surgically.

10 Claims, 4 Drawing Sheets

US 6,517,557 B1

INSTRUMENT AND USE OF INSTRUMENT FOR CORRECTING THE SHAPE OF AN EXTERNAL EAR

BACKGROUND ART

The invention concerns an instrument for correcting the shape of an external ear.

Quite a lot of people have shape external ear shapes which deviate from the average. The deformaties are of different kinds which each give the ear a characteristic shape, such as e.g. jug ears, lop ears, cop ears or Stahl's ears.

Most people with deformed ears suffer a lot from the fact that they differ from other people in such an unfortunate and conspicuous way.

Thus, jug ears can result in bantering and psychosocial problems among children and in some cases cause low self esteem. Among adults, jug ears can be a cosmetic and/or psychological problem.

Problems with protruding ears can also be of purely physical kind. Some people experience that their ears get burnt in the summer. Others have problems wearing bicycle or motorcycle helmets.

Deformed ears can be corrected surgically which also do takes place to a grear extent. About 2,000 patients with jug ears undergo operations each year in Denmark alone.

There are many different ways to operate for jug ears. Some are relatively simple, others more complicated. However, the surgical operations involve pain or soreness to some extent, this can last for a period of time of a few months to several years after the operation is performed.

Another disadvantage is that the patients after the operation must wear a bandage, which looks like a turban, for ten days in order to give the cartilage time to heal in the wanted position. Some patients furthermore have to sleep with a kind of nightcap for three weeks before the result turns up to be satisfactory.

Furthermore, an operation is usually accompanied by adverse effects. Irregular anthelix and small left cartilage prominences can thus be formed. These can be painfull and cosmetically unsatisfactory to the patient. There is furthermore a risk of infection and embarrassing scars.

A number of researches have shown that it is possible to, during the neonatal period and early childhood, permanently correct jug ears and other deformaties on the auricula in a few days merely by means of surgical tape. It is assumed that it i.a. is because of the high content of oestrogen in the blood of small children that the ear cartilage is soft and relatively easy to shape.

In order to avoid the above-mentioned disadvantages of surgically correcting jug ears, means have been developped for drawing jug ears closer to the side of the head. In these cases, any actual treatments are not done. Only a temporary, cosmetic amelioration of the ear's appearance takes place.

By way of example, a method may be mentioned in which two discs are used, the discs are attached behind the auricula and on the side of the head, respectively. When the discs then are pressed together, the ears are drawn closer to the head. This method is disclosed in the patent document WO 94/09731.

Cosmetic means of the above-mentioned kind are furthermore known from U.S. Pat. Nos. 516,135, 543,455, 1,062,654, 1,338,090, 2,339,572, 2,896,613, 3,154,071, 3,238,938, 3,695,256, 4,187,838, and 1,050,744.

The object of the invention is to provide a instrument of the kind mentioned in the opening paragraph whereby a deform ear more easily and effectively than known per se can be corrected non-invasive.

SUMMARY OF THE INVENTION

The novel and unique features according to the invention, whereby this is achieved, is the fact that correction takes place by, from two sides, affecting a chosen zone of the ear for a relatively long period of time with forces for giving the cartilage of that zone a permanent deformation.

The stress affections generates bending, stretching, and squeezing forces in the cartilage of the zone. Thereby, ruptures in the perichondrium of the cartilage are made with a subsequently appositional cartilage growth which corresponds to the perichondrium on the convex side of the bending. The cartilage thereby increases in thickness and a permanent folding of the cartilage is obtained. This effect is best obtained in early childhood.

The invention also concerns the use of an instrument for correcting the shape of an external ear. The novel and unique features according to the invention are the fact that the instrument comprises a first and a second part which are interconnected by a swing connection, and which is made to, from each side, interactingly affect a chosen zone of the ear for a relatively long period of time with forces for giving the cartilage of that zone a permanent deformation.

This instrument will stress exactly the cartilage in the chosen zone without surgical intervention whereby the aspired deformation of the ear is effectively obtained. The instrument is so easy to operate that the patient easily and conveniently can attach it to his ear himself and take it off again as required.

The instrument can furthermore be used postoperatively in stead of the conventional turban-like bandage for patients who have chosen to undergo an operation for e.g. a jug ear.

In an especially advantageous embodiment, the swing connection can be shaped as a hinge with arms which at one end are connected to either the first or the second part and at the other has a swing bed for a mutual joint pivot. The pivot can furthermore be shaped as a screw while one of the hinge beds has a female thread which fits the screw. On opposite surfaces of at least two adjacent beds, radial grooves and ribs for, when tightening up the screw, locking the arms in a chosen mutual angle position can furthermore be made alternately.

When the instrument is to be applied, the two parts are by a light manual pressure fixed around the zone where e.g. an anthelix is to be made. The position is then locked by tightening the screw. The instrument is now securely fixed on the ear. During this, its two parts are exerting a constant pressure on the cartilage of the correcting zone which thereby gradually change structure. After a space of time which can vary from a few weeks to a couple of months, the zone has thereby been forced to permanently assume the desired new shape. The ear has been corrected and the instrument can be taken off.

Naturally, the instrument can also be taken off during the correcting period for example in order to tend to the personal hygiene. Thereby, the pressure is temporarily relieved in the correcting zone but when the instrument is reattached on the ear, the above-mentioned successively structurel change process continues.

The instrument fits tightly on the ear without looking conspicuous and blemishing the appearance of the ear. The patient can therefore wear the instrument everyday without cosmetic inconveniences and even have ears which already have the desired resulting shape.

The two parts of the instrument can appropiately be a patrix and a matrix respectively for interactingly affecting the zone with forces from each side of the ear. By, from the posterior side of the ear, folding a zone between helix and concha into the matrix, which is acting on the anterior side of the ear, a permanent anthelix can be made with this construction. Cop ears can be corrected in the same way, and lop ears and Stahl's ears can be corrected by a process affecting reversely.

The cartilage in the correcting zone can have slightly different thicknesses, and it will therefore be an advantage if the above-mentioned matrix is made of a relatively thin, elastic material which allows the matrix to elastically adapt itself to the dimensions of the cartilage of the zone.

To ensure the blood supply to the ear cartilage, the inside of the matrix and the outside of the patrix can furthermore have different patterns in the shape of e.g. elevations. The best result is obtanied when the pattern on the matrix is symmetrical to the patterne of the patrix when the instrument is in its position of use.

In an especially simple embodiment, the swing connection can be a mainly U-shaped spring which advantageously can be shaped as an ear ring so that the instrument looks like an ornament.

When the two legs of the U at the same time form the first and the second part respectively of the instrument, the two parts of the instrument can have effect from the same side of the ear.

The invention will be explained in greater details below, describing only exemplary embodiments with reference to the drawing, in which

DETAILED DESCRIPTION OF THE PREFERRED EMBODIMENT

Figure 1:
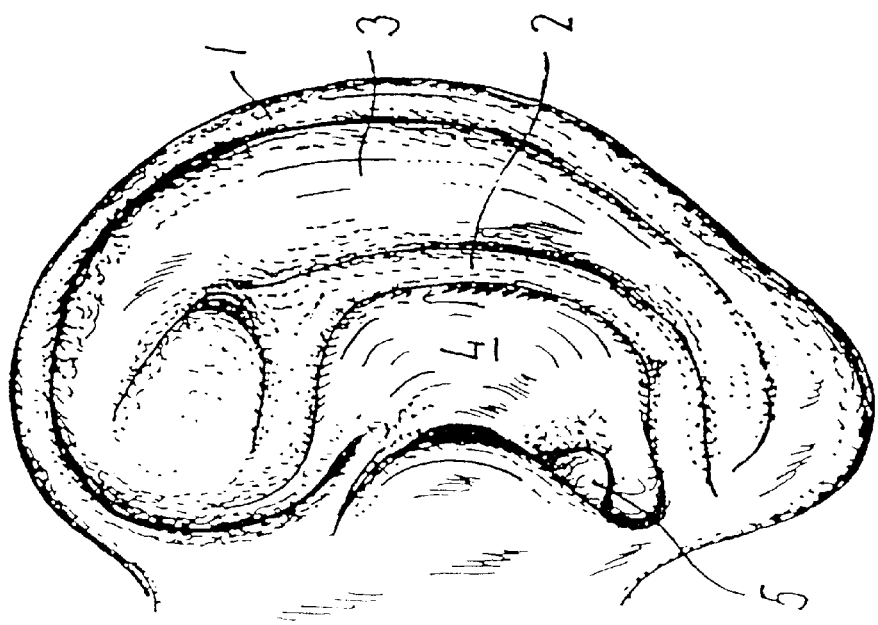
FIG. 1 shows a normal ear.

FIG. 1 shows a normal ear with the external fold, helix 1 and the fold in front of helix, anthelix 2. On the ear is furthermore scarpha 3 which is the furrow between helix and anthelix, and concha 4 which is the infundibular groove right in front of the external meatus 5.

Figure 2:
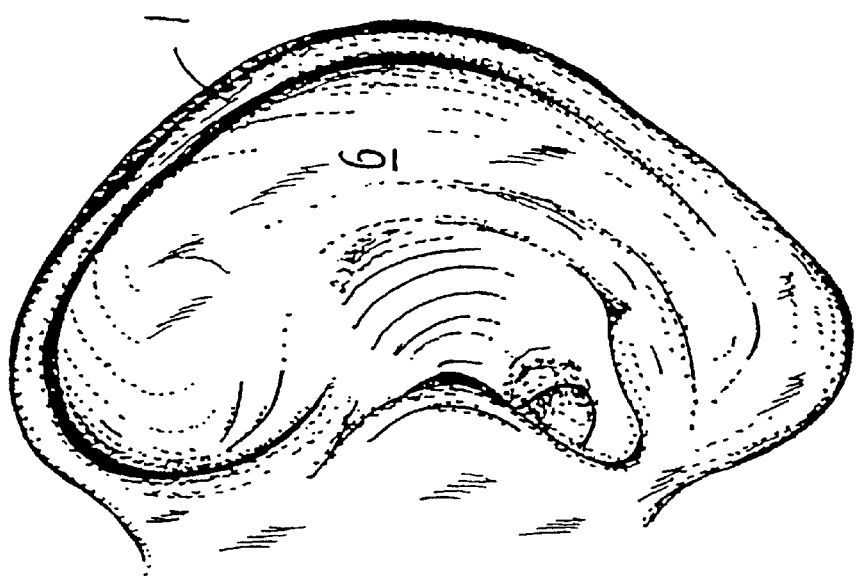
FIG. 2 shows a jug ear with missing anthelix.

FIG. 2 shows a jug ear characterised in that the normal existing anthelix is not present in the area 6. This deformaty is in different ways to the considerable inconvenience of the respective patient and it is therefore desirable to form an anthelix in the area 6.

Figure 3:
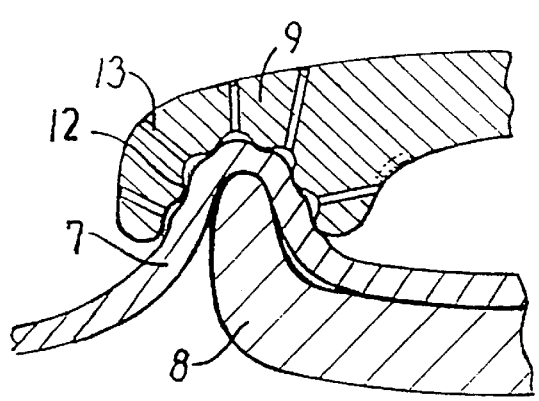
FIG. 3 is a fragmentarily cross sectional view of a first embodiment of a instrument according to the invention attach on a jug ear.
Figure 4:
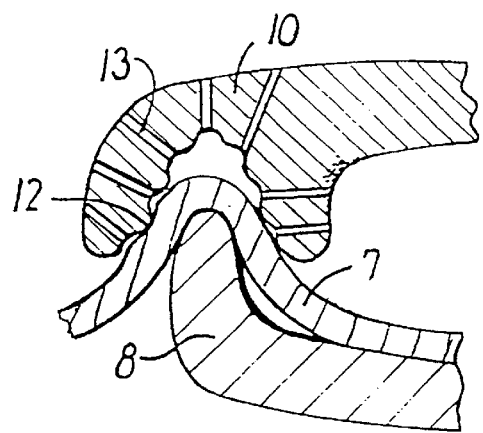
FIG. 4 is a fragmentarily cross sectional view of a second embodiment of a instrument according to the invention attach on a jug ear.

This anthelix is formed by, as shown in FIGS. 3 and 4, compressing a zone 7 of the area 6 between a posterior acting patrix 8 and an anterior acting matrix 9 (FIG. 3) and 10 (FIG. 4) so that a fold 11 is made.

Figure 5:
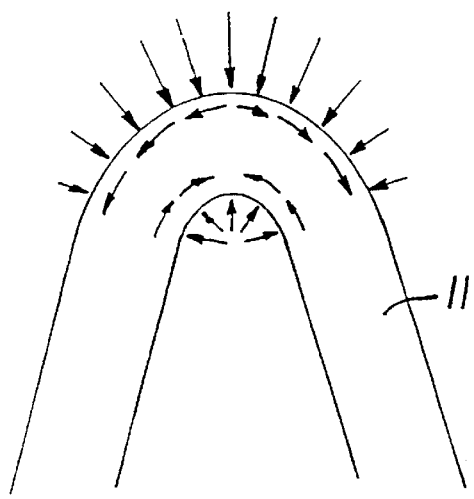
FIG. 5 is a diagrammatic view on a larger scale of the stress condition in a zone of the ear cartilage under the influence of the instrument shown in FIG. 3 and 4.

Thereby, is the stress condition shown in FIG. 5 in the cartilage of the zone initiated. The patrix and the matrix compress the cartilage of the fold 11 transversely with posterior and anterior acting compressive forces respectively as indicated by the arrows. Lengthwise of the cartilage of the fold, compressive forces are at the same time initiated on the outside and on the inside as indicated by the arrows. The stress concentration is largest at the inner and outer summit respectively of the fold.

The tensions in the cartilage compress and stretch the cartilage in dependence of the amount and direction of the stress. These deformations which at short-period loading generally speaking are elastic will over a longer period gradually assume character of permanent deformations. Thereby, the folding of the cartilage becomes permanent and when the instrument is taken off the ear, the fold will remain and form a proper anthelix. The jug ear has thus been easily and painlessly corrected and as it will appear, without the disadvantages which follows of a surgical operation.

To ensure the blood supply to the ear, the matrix has a number of elevations 12 in the shape of e.g. wavy ribs. The exterior of the ear is freely extending, as shown, between the elevations without touching the inside of the matrix, and these free areas are therefore not stressed as much as the surrounding areas.

The bottom of the elevations furthermore communicates with open air via a number of holes 13 through which the ear skin can breathe.

The holes furthermore ensure that an positive pressure is not generated between the outside of the fold 7 and the matrix when this and the patrix are tightened together around the fold.

The outside of the patrix is smooth in the shown case, but the patrix can as the matrix have elevations and breathing holes. The need for these is however not as great as is the case of the matrix because the patrix has a far smaller area in contact with the inside of the fold.

In FIG. 3, the matrix 9 has an inner side of a shape which corresponds to the complementary shape of the exterior of the anthelix.

In FIG. 4, the inner side of the matrix 10 has, seen from a sectional view, a more pointed shape. Thereby, the matrix will not abut on the outside of the fold with the bottom, but only with some of the sides. The advantage of this structure is that the matrix can be applied on ears with different ear cartilage thicknesses. The area of action of the matrix is merely moved more or less up along the sides of the matrix in dependence on the thickness of the respective ear cartilage. The instrument is therefore flexible in this embodiment. Furthermore, it affects the ear cartilage in the fold with stress forces which serve for advantageously keeping the cartilage stretched so that the correcting process is expedited.

By the above-described process, a permanent fold in the shape of an anthelix was made on a jug ear.

Figure 6:
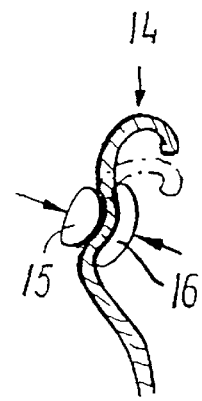
FIG. 6 is a cross sectional view of how a jug ear is corrected by means of the instrument according to the invention.

FIG. 6 shows how a lop ear 14 is corrected by means of the instrument according to the invention. The lop ear is characterised in that is has a fold which is not present on a normal ear. The fold has the effect that the top of the ear is hanging down, as indicated with a broken line. Correction therefore takes place by straightening the unwanted fold so that the ear is unfolded as indicated with a full-drawn line.

For this purpose, a patrix 15 is placed on the outside of the fold and a matrix 16 on the inside. The two parts 15 and 16 are compressed around the fold as indicated by the arrows. Thereby, the fold is deformed in the opposite direction whereby the top part of the ear is raised. The stress of the instrument on the ear will, in the same way as mentioned earlier, successively give the ear cartilage a permanent deformation. When the instrument is taken off, the ear will therefore mainly remain upright in the forced position. The ear shape has been corrected.

Figure 7:
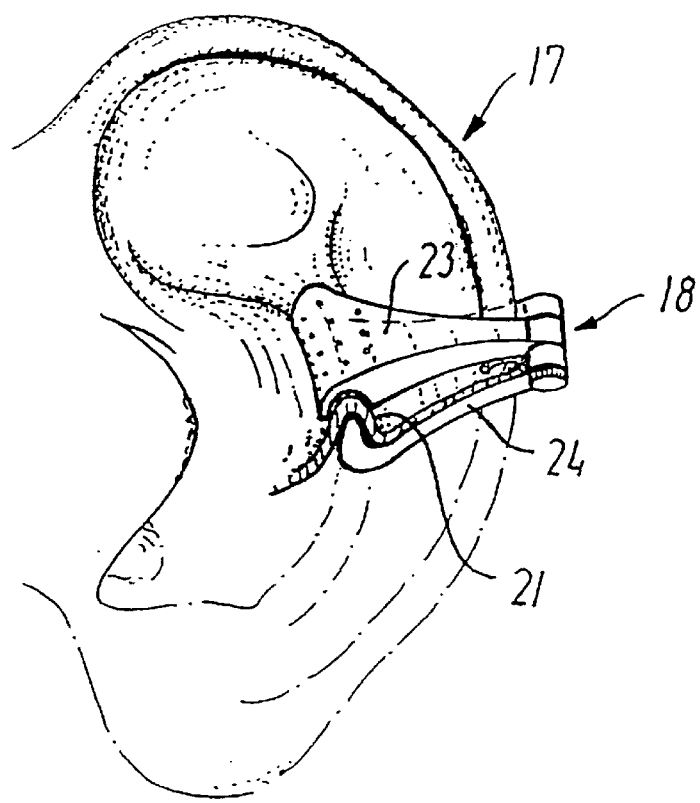
FIG. 7 is a perspective view partly in section of a instrument according to the invention attached on an ear which is to be corrected for missing anthelix.

In FIG. 7 is seen a jug ear 17 which is being corrected for missing anthelix by means of a preferred embodiment of a instrument 18 according to the invention. The figure is somewhat incorrectly drawn as the upper part of the instrument is shown normally from the front of the ear while the bottom part is shown on a section through the ear for the sake of lucidity.

Figure 8:
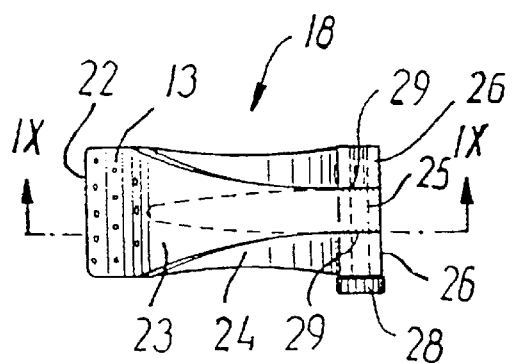
FIG. 8 shows the instrument shown in FIG. 7, seen from above.
Figure 9:
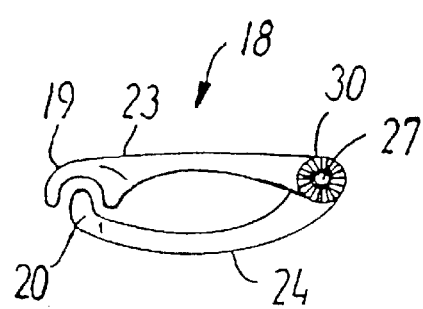
FIG. 9 is the same but seen from the side, partly in section.

The instrument, which also is shown in FIGS. 8 and 9, has a matrix 19 and a patrix 20 for, by compression, forming a fold 21 in the area without anthelix in the jug ear and thereby forming an anthelix in the way mentioned earlier and with reference to FIGS. 3, 4, and 5.

The matrix and the patrix 19 and 20 are each placed at the end of arms 23 and 24 of a hinge 22. At the other end, the arm 23 has a swing bed 25 and the arm 24 a swing bed 26. The arms 23 and 24 can swing around a mutually joint pivot 27 which in this case is shaped as a screw 27 with a grip-head 28 for tightening the screw. In the swing bed 26 opposite to the grip-head, a female thread has been made which fits the thread of the screw.

On opposite surfaces 29 on two adjacent beds, a coupling 30 is made which consists of complementary shaped ribs and grooves on the mentioned opposite surfaces 29.

At first, the screw is not tightened. The arms with the matrix 19 and the patrix 20 respectively can therefore freely swing around the pivot or the screw 27. The matrix and the patrix are then moved into a position in the area where an anthelix is to be formed, and compressed by a light finger pressure so that the patrix compresses the area into a fold in the matrix. Finally, the screw 27 is tightened by turning the grip-head 28 with the fingers. The coupling 30 thereby locks the arms 23 and 24 in the mutual angle position in which the fingers have placed them. The instrument has now quickly, easily and securely been attached to the ear where it now is performing the earlier mentioned correcting function.

In a variant of this embodiment which is not shown, the coupling is a claw coupling which normally is held in engagement by a spring mechanism. When the matrix and the patrix of the instrument, with the fingers, are compressed around the area where an anthelix is to be made, the claw coupling automatically locks the instrument in the chosen position. When the spring mechanism is released, the instrument can easily be opened and taken off. This structure is especially easy and convenient to handle.

Figure 10:
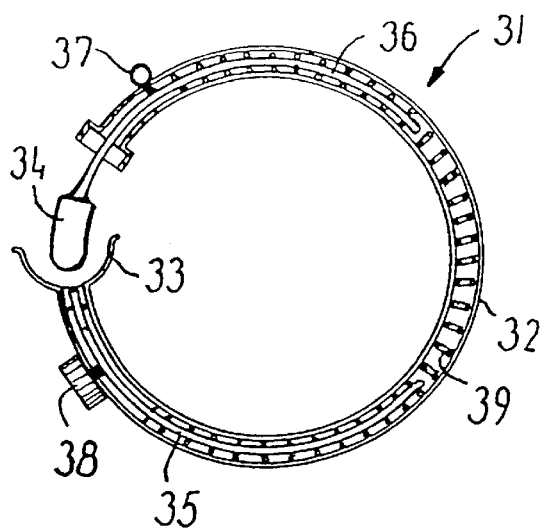
FIG. 10 is a view from the side and partly in section of an embodiment of an instrument according to the invention in the shape of an ear ring.

FIG. 10 shows an embodiment of a instrument 31 which besides its correcting function also has a cosmetic advantage as it looks like an ear ring.

The instrument 31 comprises a bend tube 32. The tube can, as shown, be extended along a circle, but the configuration can also be of any suitable kind, for example triangular or oval.

The patrix 34 is fitted at the end of a bar 36 which has the same curvature as the tube. The matrix 33 is fitted to the other end of the tube. The patric 34 can with its bar be displaced relative to the tube by working a knob 37 on the bar 36 of the patrix and which is extending through a longitudinal slit (not shown) in the tube wall.

A pretightened spiral spring 39 in the tube 32 presses the bar 36 with the patrix 34 towards the matrix 33. The spring force can be regulated by means of another knob 38 which also is extending through the not shown slit in the tube wall. On the internal end of the knob, an abutment 35 is placed which abuts on the spring end. The spring force is regulated in size by displacing the knob 38 back and forth in the not shown slit so that the spiral spring is tightened more or less.

When the instrument shown in FIG. 10 is to be employed, the patrix 34 is pulled free of the matrix 33 by working the knob 37 so that the patrix and the matrix can pass over the ear and be moved into position above the area where a permanent deformation is desired. The knob 37 is then gently relinquished after which the instrument works in the same way as described in the other embodiments.

Figure 11:
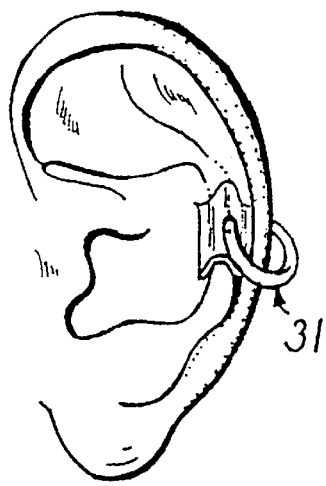
FIG. 11 is the same fixed on an ear.

FIG. 11 shows that the instrument in this embodiment looks like an ear ring when it is fixed on an ear.

Figure 12:
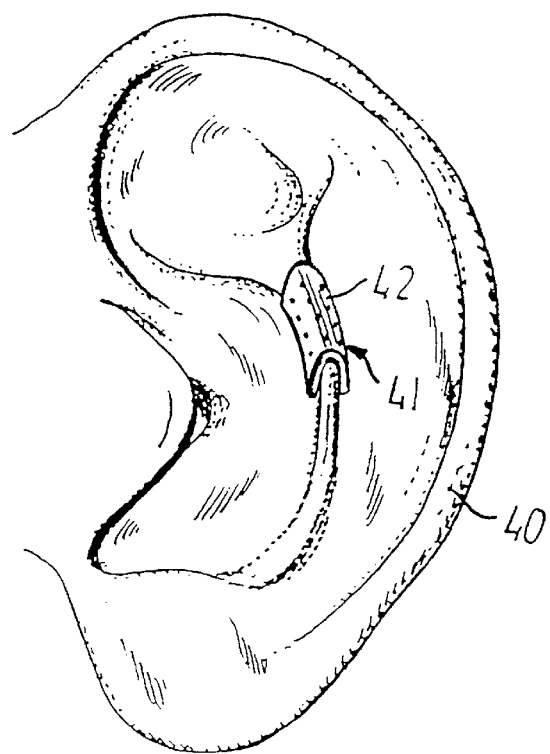
FIG. 12 shows a jug ear with an embodiment of an instrument according to the invention in the shape of a clip.

FIG. 12 shows a jug ear 40 which is corrected by means of a further embodiment 41 of the instrument according to the invention. This structure is especially simple as it merely consists of a U-shaped, elastic clip which in use is placed on the ear where is desired to form an anthelix. The clip can be made of a relatively thin, elastic sheet with breathing holes 42.

In all of the cases, at least the instrument surfaces in contact with the ear can advantageously be coated with an allergy tested, elastic material, such as e.g. silicone, polyethylene or foam.

The instrument can advantageously be made of a flexible plastic chosen among the group of e.g. Plexiglass, polyethylene, alkyde plastics, polystyrene, polyamide plastics, melamine plastics, PVC, polyestere, thermoplastics, carbonate plastics, polypropylene, polyoxymethylene plastics, ether plastics, foam, silicone foam, Reston foam, silicone.

The employed plastic can furthermore be of the kind which at least partly can be permanently deformed. Thereby, the acting parts of the instrument can manually be adapted to an individual ear.

The instrument can also entirely or partly be made of metal, such as e.g. spring steel, stainless steel, titanium, aluminium, zinc, nickel, and brass. The employed metal can furthermore be coated with a plastic from the above group.

The embodiments of the instrument as shown in the drawing and described above are only by way of example. Many other embodiments are possible within the scope of the invention.

The instrument can thus merely consist of two parts which are compressed on the ear area which is to be given a permanent deformation by means of one or more screws led through premade holes in the ear.

What is claimed is:

1. An instrument for correcting the shape of an external ear, said instrument comprises a first and a second part, wherein said parts are interconnected by a swing connection, and made to, from each side, interactingly affect a chosen zone of the ear for a relatively long period of time with forces for giving the cartilage of the zone a permanent deformation.

2. An instrument according to claim 1, wherein the first and the second part are a patrix and a matrix respectively for interactingly affecting the zone with forces from each side of the ear.

3. An instrument according to claim 2, wherein the matrix is made of a relatively thin, elastic material and has a mainly U- or V-shape.

4. An instrument according to claim 2, wherein the inside of the matrix and the outside of the patrix is provided with different patterns in the shape of for example elevations, and that the pattern of the matrix is mainly symmetrical to the pattern of the patrix when the instrument is in the position of use.

5. An instrument according to claim 1, wherein the swing connection is shaped as a hinge with arms which at one end are connected to either the first or the second part and which at the other end has a swing bed for a joint pivot, that the pivot is shaped as a screw while one of the beds of the hinge has a female thread fitting the screw, and that opposite surfaces on at least two adjacent beds have locking means for locking the arms in a number of prechosen mutual angle positions when the screw is tightened.

6. An instrument according to claim 1, wherein the locking means are made up of alternating radial grooves and ribs made on the opposite terminal surfaces of at least two adjacent beds.

7. An instrument according to claim 1, the swing connection is a mainly U-shaped spring wherein the two legs of the U form the first and the second part respectively of the instrument for correcting the shape of the an external ear.

8. An instrument according to claim 1, wherein the swing connection is shaped as an ear ring.

9. Use of an instrument according to any claim 1, wherein a correction takes place by, from two sides, affecting a chosen zone of the ear for a period of time with forces for giving the cartilage of the zone a permanent deformation.

10. A method for correcting the shape of an external ear, wherein correction takes place by, from two sides, affecting a chosen zone of the ear for a period of time with forces for giving the cartilage of the zone a permanent deformation.

* * * * *